United States Patent [19]

Isaacson

[11] 4,382,199
[45] May 3, 1983

[54] HYDRODYNAMIC BEARING SYSTEM FOR A BRUSHLESS DC MOTOR

[75] Inventor: Milton S. Isaacson, Dayton, Ohio

[73] Assignee: Nu-Tech Industries, Inc., Dayton, Ohio

[21] Appl. No.: 204,624

[22] Filed: Nov. 6, 1980

[51] Int. Cl.³ ............................ A61F 1/24; H02K 5/12
[52] U.S. Cl. .......................................... 310/87; 3/1.7;
310/90; 416/111; 417/423 R; 384/107
[58] Field of Search ........................ 310/90, 66, 82, 80,
310/87; 3/1.7; 318/696; 128/1 D, 260;
308/DIG. 3, 36, 122, 123, 9, 10; 74/5.43;
290/52; 415/110–112, 503; 417/423 R

[56] References Cited

U.S. PATENT DOCUMENTS

| | | | |
|---|---|---|---|
| 2,916,642 | 12/1959 | Macks | 310/90 |
| 2,983,832 | 5/1961 | Macks | 310/90 |
| 3,433,986 | 3/1969 | Arutunoff | 310/90 |
| 3,446,150 | 5/1969 | Dee | 310/90 |
| 3,951,573 | 4/1976 | Dunning et al. | 417/424 |
| 4,027,215 | 5/1977 | Knight et al. | 318/341 |
| 4,173,796 | 11/1979 | Jarvik | 3/1.7 |
| 4,277,706 | 7/1981 | Isaacson | 310/80 |

Primary Examiner—J. D. Miller
Assistant Examiner—D. L. Rebsch
Attorney, Agent, or Firm—Wood, Herron & Evans

[57] ABSTRACT

A hydrodynamic bearing system for a motor. The motor is illustrated and described as driving a pump for an artificial heart. The motor stator has a cylindrical bore which is closed at one end. The rotor is slidable and rotatable in the bore. The rotor has affixed to its shaft an impeller with its outside diameter concentric to the rotor outside diameter. Both rotor and impeller are supported hydrodynamically such that the tendency is for the entire rotor/impeller assembly (the only moving element) to be completely suspended by fluid. The rotor can be rapidly reversed to provide heart pumping action or can be driven unidirectionally for artificial heart pumping action of another type. The fluid cannot easily escape from the closed end of the stator, thereby providing a dashpot effect which tends to keep the rotor from changing position. In moving away from the closed end, the rotor brings fluid between the end of the rotor and the closed end of the bore to act as a buffer or bearing fluid when reversal moves the rotor toward the closed end.

4 Claims, 3 Drawing Figures

HYDRODYNAMIC BEARING SYSTEM FOR A BRUSHLESS DC MOTOR

This invention relates to a motor, and more particularly, to a hydrodynamic bearing for a brushless DC motor.

The invention will be described in particular relation to its use in an artificial heart or in a left ventricle assist device (LVAD), but it should be understood that the hydrodynamic bearing concept utilized by the invention will have wider application. A LVAD generally of the type contemplated by the present invention is illustrated in application Ser. No. 30,280, filed Apr. 16, 1979.

In the currently developing LVAD or artificial heart technology, there is need for a motor driven axial flow pump (energy converter) to hydraulically actuate a blood pump to circulate the blood throughout the body. The package of energy converter and blood pump is for implantation in the body with the intention, or at least the hope, that it remain in the body for the rest of the patient's life. Obviously, it is desirable for the energy converter to be the smallest, lightest, most reliable, longest lasting and most efficient device possible. A sacrifice of any of these requirements will result, at the least, in an inconvenience to the patient and at the most in substantial impairment of the patient's ability to function.

The function of the energy converter is to drive a blood pump in such a way as to simulate heartbeats. At present, it is contemplated that the most appropriate energy converter will contain a brushless DC motor of the type disclosed in U.S. Pat. No. 4,027,215. The present invention contemplates a motor whose dimensions are no greater than approximately ¾ inch outside diameter and 1.75 inches long. The motor is programmed to reverse typically every 0.3 seconds simulating 100 heartbeats per minute. At each reversal, the motor changes from typically 10,000 rpm in one direction to 10,000 rpm in the opposite direction, the reversal occurring in approximately 25 milliseconds. Over 100 million cycles at the 100 beats per minute will be required over a two year period.

It is contemplated that the rotor will carry an impeller which will drive a low viscosity liquid first in one direction and then in the opposite direction, that liquid flowing into a diaphragm and causing an alternate pumping of the patient's blood. The nominal value of the axial thrust load seen by the rotor bearings is calculated to be about 1.25 lbs. when the corresponding aortic pressure is 100 millimeters of mercury. For high output, corresponding to an aortic pressure of 125 millimeters of mercury, the thrust force is calculated to be 1.6 lbs. For a reverse flow in which the aortic pressure may be one-fourth the forward pressure, the thrust loads for the nominal low output will be proportionally 0.31 lbs.

An objective of the present invention has been to provide a hydrodynamically stable (no half speed whirl or conical whirl) bearing system between the rotor and stator and between impeller tips and bore which will withstand the thrust loads described as well as the minimal radial loads encountered over the life of the system.

This objective of the invention is attained by providing a stator having a cylindrical bore which is closed at one end. A cylindrical rotor passing through the open end of the stator is axially and rotatably mounted in the bore. In the pumping application which has been discussed, the rotor carries a bladed impeller that is axially and rotatably mounted in its bore. The whole assembly is immersed in the fluid which is to be pumped by the impeller. The rotor/impeller combination is supported hydrodynamically, seeking a position of equilibrium within the two bores.

The position of equilibrium of the rotor with respect to the stator is maintained by the hydrodynamic effects of the fluid which provides the radial and axial bearing support of the rotor with respect to the stator; the dashpot effect which maintains a film of fluid between the rotor and the closed end of the stator so as to maintain the rotor centered axially as well as resisting axial movement in either direction; and a squeeze film effect which minimizes the possibility of rotor-to-stator contact during those periods of almost infinitesimal time when the rotor is stopped during reversal, all as will be described below.

In summary, whereas it is conventional to mount a rotor in a stator with bearings at each end of the stator, in the present invention the bearings are formed by the fluid in the gap between the rotor and stator.

The control circuit for electronically commutating the motor and reversing it is carried inside the body with the main battery power supply outside the patient's body.

The several features of the invention will become more readily apparent from the following detailed description taken in conjunction with the accompanying drawings in which.

Figure 1:
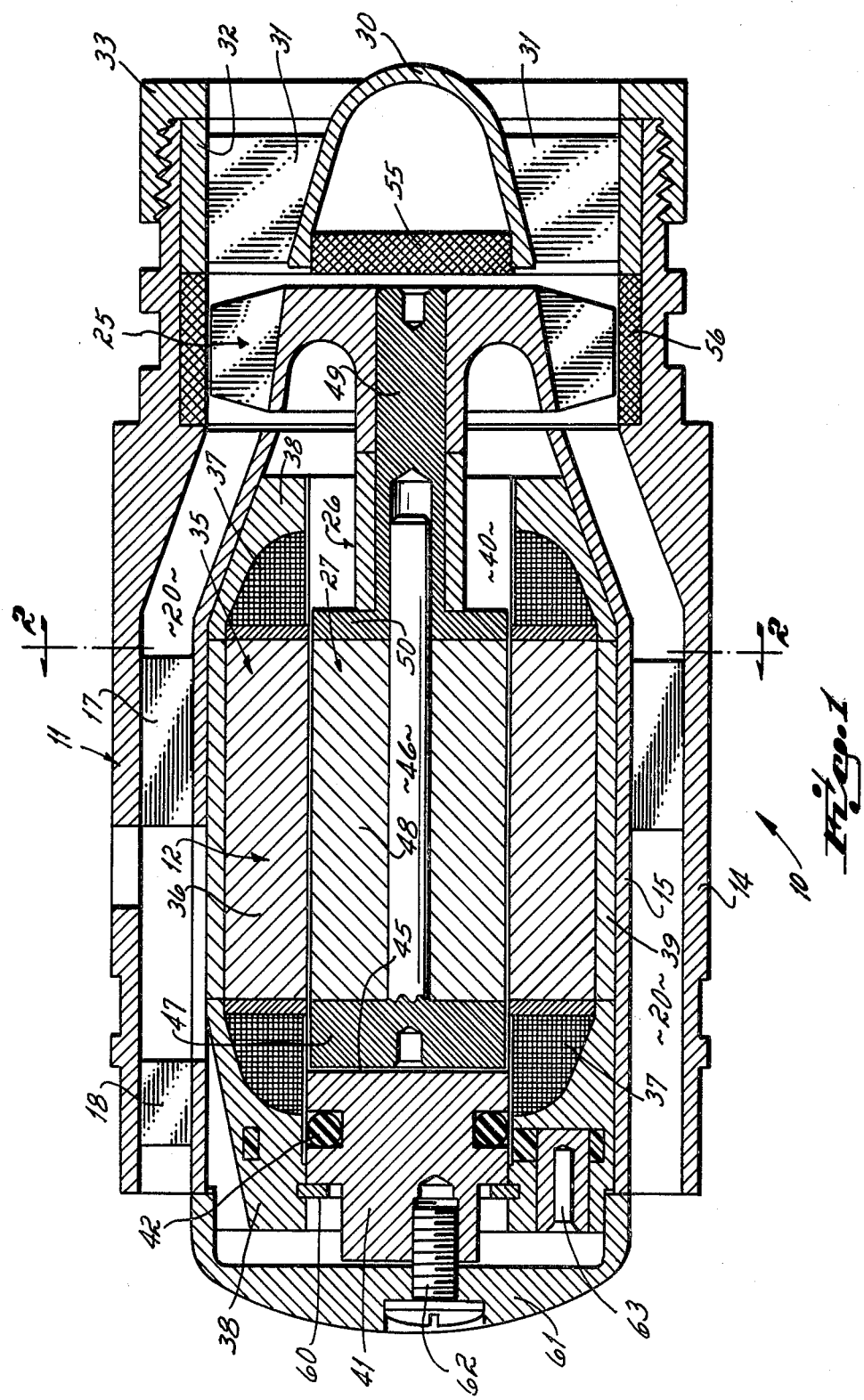
FIG. 1 is a cross-sectional view of the motor and pump.
Figure 2:
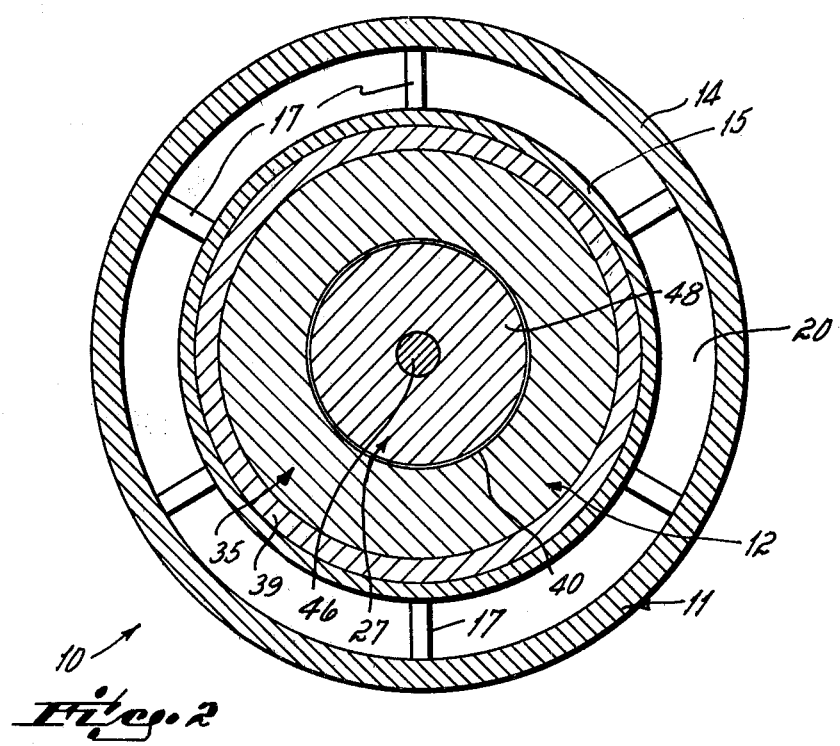
FIG. 2 is a cross-sectional view taken along lines 2—2 of FIG. 1.

The pump of the present invention is shown at 10 in FIGS. 1 and 2. It includes a housing 11 within which the motor 12 is mounted. The housing is generally cylindrical and has an outer sleeve 14 and an inner sleeve 15. The outer and inner sleeves are maintained in spaced relation by six vanes 17 spaced equiangularly around the circumference of the sleeve and three struts 18, also spaced equiangularly around the housing. The space between the two sleeves forms a passageway 20 for a fluid which may be a gas or liquid, but preferably a low viscosity hydraulic fluid. The fluid is pumped through the passageway by an impeller 25 which is fixed to a shaft 26 on a rotor 27 of the motor 12.

Adjacent the impeller is a nose cone 30 connected by vanes 31 circumferentially spaced around the nose cone to a ring 32. The nose cone 30 and ring 32 are held securely onto the housing by a flanged collar 33 which is threaded onto the end of the outer sleeve 14 adjacent to the impeller.

In addition to the rotor, the motor includes a stator 35 which is built up in the central portion 36 thereof by laminations of ferro-magnetic material and is provided with coils 37 which create the magnetic field. The stator is secured in the central portion of the housing by means of an epoxy encapsulent 38 at the ends of the stator, the stator being centered in the housing by a yoke ring 39.

The stator has an axial bore 40 which is closed at one end by a plug 41 and sealed by an O-ring 42. The plug may be made of stainless steel. It has a surface 45 facing into the bore 40 which may be planar or may be slotted with something in the nature of Rayleigh steps to facilitate the creation of a hydrodynamic thrust bearing, as will be discussed below. See Fuller "Theory and Practice of Lubrication Engineers," John Wiley & Sons, Inc.

The rotor has an integral shaft 46 and disk 47 at its inner end onto which are mounted the magnetic pole elements 48 which in conjunction with the rotating field created by the coils 37 cause the rotor to rotate within the bore.

At the other end of the rotor is a second shaft 49 which is fixed to the shaft 46 and terminates in an annular flange 50. The shaft and disk plate 47, as well as the shaft 49 and flange 50, may be formed of stainless steel or beryllium copper alloy.

The surface of the disk 47 facing the plug 41 is preferably plated with a tin-lead alloy or other similar soft bearing material such as babbitt so that if there is some misalignment present, the soft material will be self-lapping and will eventually achieve a perfectly flat surface. Further, when the fluid film breaks down, as upon starting, or heavy shock, an acceptable bearing surface will prevent seizing and the like. The cylindrical surface of the rotor is also preferably plated with a thin coating of bearing material such as tin-lead alloy, graphite or babbitt.

The outside diameter of the rotor 27 is preferably about 0.0006 inch less than the inside diameter of the stator bore 40. It can be seen that the fluid flowing through the passageway 20 will also fill the bore 40 and provide a hydrodynamic bearing between the respective cylindrical surfaces on the stator and rotor as well as the facing surfaces of the plug 41 and disk plate 47. The gap between the rotor cylindrical surface and the bore cylindrical surface should be maintained as small as possible, e.g., 0.0003 inch, for three reasons. First, the smaller the gap, the smaller the magnetic reluctance between the stator and rotor and hence the more power that can be generated by the motor with a given electrical input.

Second, it can be seen that there is nothing in the assembly to mechanically center the rotor within the stator. If the gap between the rotor and stator is large, then when the motor is at rest the rotor will be pulled magnetically to one side of the stator. The larger the gap, the larger will be the eccentricity between the rotor and stator at start-up.

Finally, it is a feature of the invention to create a hydrodynamic thrust bearing between the plug 41 and the disk plate 47. Initially, hydraulic fluid will be introduced into the space between the plug and plate. That fluid can only escape by passing through the gap between the rotor and stator. The smaller the gap, therefore, the greater dashpot effect which maintains the rotor axially centered, against forces in either direction, within the stator and minimizes the opportunity for the rotor to bottom out against the plug 41 when the thrust forces drive the rotor toward the plug 41.

It is desirable to orient the motor in the direction wherein the greatest thrust forces tend to drive the rotor toward the plug 41. Because of the possibility that the rotor might be caused to move axially toward the nose cone 30, it is also desirable to provide a bearing-type surface such as tin-lead graphite or babbitt in the form of a plug or plated disk 55 at the inner side of the nose cone 30 against which the impeller can rub should there be a fluid film breakdown. It should be understood that a fluid film normally exists between the impeller 25 and the disk 55 to provide substantially the same hydrodynamic bearing effect and squeeze film effect which exists between disk 47 and plug 41. Additionally, a plated ring of tin-lead, babbitt or graphite is placed in the form of a ring 56 surrounding the impeller tips so as to minimize any possibility of damage or failure by the contact of the impeller tips with the inner surface of the housing 11. The clearance between the blade tips and the inside diameter of the ring 56 is about 0.0003 inch. The manufacturing clearance is about 0.0001 inch with initial wear creating the 0.0003 minimal working clearance.

At the plug end of the motor, the plug is secured to the encapsulation 38 by a snap ring 60 or the like. A cap 61 is secured to the plug and thence to the housing by means of a screw 62. Four terminals 63 are provided in the encapsulation at the plug end of the housing, the terminals being connected to the coils 37 for the electrical energization of the stator to create the rotating field.

Figure 3:
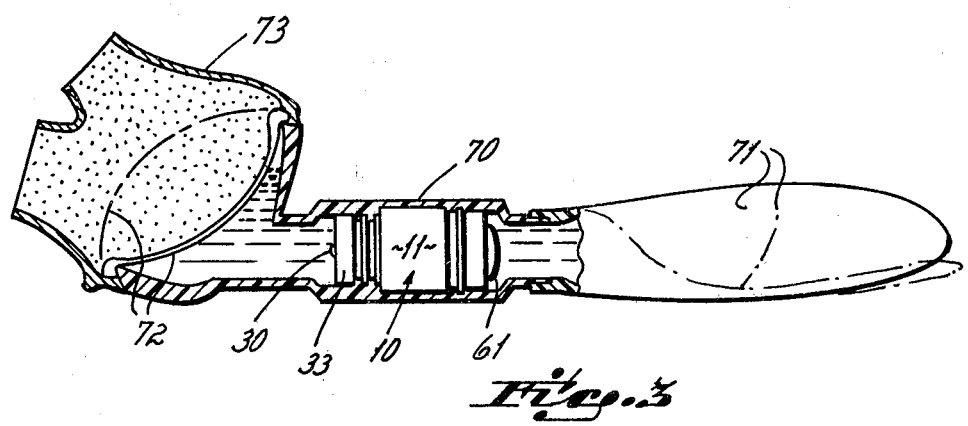
FIG. 3 is a diagrammatic view of the pump in association with a heart assist device.

The device as described can be employed as a unidirectional motor, but preferably the motor is designed as a reversible motor. The environment for which the motor is intended, namely, that of a pump in an artificial heart for a left ventricle assist device, is illustrated in FIG. 3. In that environment it is intended that the motor operating as a brushless DC motor with circuitry of the type disclosed in Patent No. 4,027,215 will run at 10,000 rpm in one direction and change to 10,000 rpm in the opposite direction, the reversal occurring in approximately 25 milliseconds.

As shown in FIG. 3, the pump 10 is mounted in a housing 70. At one end of the housing, a soft plastic reservoir sack 71 is connected to the housing. At the other end of the housing, a diaphragm 72 encloses the housing. The housing and diaphragm 72 are connected to a blood chamber 73. The motor is preferably oriented in the housing so that the impeller is directed toward the diaphragm, the systolic or higher pressure flow being generally toward the left as viewed in FIG. 3.

The condition of the system shown in full lines is generally as it would appear at the end of the diastolic flow wherein the reservoir sack is filled and the diaphragm 72 has moved toward the motor and pump. Upon reversal of the motor, the pump drives the diaphragm toward the left to the broken line position. The movement of the hydraulic fluid within the sack and system has moved toward the left to force the diaphragm to the left, at the same time collapsing the hydraulic reservoir sack.

In the operation of the invention, with a balanced rotor and impeller, the radial loads will be very low. The nominal thrust loads will be approximately 0.3 to 1.25 pounds and will be applied alternately in forward and reverse directions. The reversal can be effected extremely rapidly, changing from 10,000 rpm in one direction to 10,000 rpm in the opposite direction in approximately 25 milliseconds. The time during which the rotor of the motor is turning at a speed below 1,000 rpm is minimal, being approximately one millisecond. There is, therefore, a substantially constant hydrodynamic effect between the cylindrical surfaces of the rotor and stator, respectively, which maintains the rotor centered within the stator and riding on the low viscosity hydraulic fluid which is preferably DC 200 oil (a methyl silicone oil whose viscosity is 1.5 centistokes) or water.

When the rotor is inserted into the stator, immersed in fluid, it takes a very substantial amount of time for the oil in the dead end space between the plug 41 and the plate 47 to be squeezed out through the very narrow gap between the rotor and the stator (the dashpot effect).

When the rotor is fully inserted, the disk 47 may contact the plug 41. In operation, however, contact may never occur. Each time the motor is reversed, the change in direction of flow on the impeller causes a thrust load which attempts to displace the rotor axially. Because of the dashpot effect, motion in either direction is greatly damped due to the time required for a finite volume of hydraulic fluid to ooze between the very narrow gap. The axial flow pump is designed so that the greater thrust forces (systolic flow) tend to displace the motor rotor in the direction of the plug 41.

A fluid film separates the plug 41 from the end of the rotor and a finite amount of time is necessary for this cushioning fluid film to be squeezed away. When the rotor is reversed, the forces are reversed, and rather than squeezing the fluid out of the gap between the plug and the rotor, more fluid is drawn in. Thus, on the subsequent reversal, the fluid film between the plug and the rotor is reestablished. In all likelihood, no contact between the rotor and the plug or thrust bearing will occur.

The hydrodynamic forces which keep the rotor centered and out of contact with the stator are a function of diameter, speed, surface finish and other variables. If rotation is stopped, the magnetic forces of the motor will pull the rotor to one side if it is the slightest bit out of center. However, the time during which the motor is stopped is very brief. A squeeze film effect prevents contact during this period of time. The squeeze film works as follows. If an object is laid on top of a fluid, the object will tend to fall through the fluid toward the surface below. However, before it can make contact, it must squeeze the liquid out of the ever-narrowing gap between the two surfaces. This takes a finite amount of time and the time can be calculated knowing the forces drawing these surfaces together, knowing the surface areas and distances involved, and knowing the fluid viscosity. It is believed that with the very short reversal time and particularly the extremely short time during which there is no movement of the rotor with respect to the stator, the squeeze film effect will prevent metal-to-metal contact.

There is additional hydrodynamic centering force at play between impeller tips and bore to help support the rotor/impeller assembly and to stabilize it against half speed whirl and conical whirl. The blade tips and adjacent openings form the geometry that creates the hydrodynamic film for supporting the impeller.

In summary, the motor of the present invention employs squeeze film effects, dashpots effects and hydrodynamic effects, all of which combine and cooperate to prevent metal-to-metal contact between the rotor and the stator and to lubricate the rotor as it rotates within the stator.

Having described my invention, I claim:

1. A motor comprising,
   a fixed stator having a cylindrical bore providing a bearing surface, said bore being closed at one end,
   a cylindrical rotor rotatably and slidably mounted in said bore, forming with said bore a journal bearing,
   said rotor having an inner end cooperating with the closed end of said bore to form a thrust bearing,
   a fluid between said rotor and said cylindrical bore, including said closed end, said fluid acting hydrodynamically with said thrust bearing and said journal bearing to minimize metal-to-metal contact,
   an impeller mounted on said rotor,
   means for cyclically reversing the direction of said rotor,
   said impeller imparting a greater thrust load toward said closed end of said bore when said impeller rotates in a first direction than the thrust load in the opposite direction when said impeller is reversed,
   the outside diameter of said rotor being only slightly less than the inside diameter of said bore, thereby creating a dashpot effect tending to resist said rotor's engagement with the closed end of said bore on reversal of said impeller.

2. A motor as in claim 1 in which said rotor and closed end of said stator present opposed facing surfaces, one of said surfaces being configured to increase the hydrodynamic capability of said fluid to resist thrust forces tending to bring said surfaces into contact.

3. A motor as in claim 1, said motor being immersed in a low viscosity liquid, said liquid acting hydrodynamically with said thrust bearing and said rotor journal bearing.

4. A motor as in claim 1 in which the outside diameter of said rotor is about 0.0006 inch less than the inside diameter of said bore, thereby creating in conjunction with a closed-off end of the stator bore a dashpot effect tending to resist axial movement of said rotor in said bore.

* * * * *